United States Patent [19]

Lott

[11] Patent Number: 5,038,778
[45] Date of Patent: Aug. 13, 1991

[54] ENDOTRACHEAL TUBE TAPE

[76] Inventor: Mark B. Lott, P.O. Box 1255, Tifton, Ga. 31794

[21] Appl. No.: 391,296

[22] Filed: Aug. 9, 1989

[51] Int. Cl.⁵ .............................................. A61M 16/00
[52] U.S. Cl. ........................ 128/207.17; 128/DIG. 26
[58] Field of Search .................. 128/207.17, DIG. 26, 128/155; 604/179, 180; 24/DIG. 11

[56] References Cited

U.S. PATENT DOCUMENTS

| | | | |
|---|---|---|---|
| 1,555,960 | 10/1925 | Fuller | 128/155 |
| 2,005,676 | 6/1935 | Hanover | 24/DIG. 11 |
| 2,646,040 | 7/1953 | Stanton | 128/155 |
| 3,146,778 | 9/1964 | Krawiec | 604/180 |
| 3,161,199 | 12/1964 | Shaw et al. | 604/179 |
| 3,430,300 | 3/1969 | Doan | 128/DIG. 26 |
| 3,677,250 | 7/1972 | Thomas | 128/DIG. 26 |
| 3,713,448 | 1/1973 | Arrott | 128/DIG. 26 |
| 3,927,676 | 12/1975 | Schultz | 128/DIG. 26 |
| 4,622,034 | 11/1986 | Shattuck | 128/DIG. 26 |
| 4,822,342 | 4/1989 | Brawner | 128/DIG. 26 |
| 4,915,102 | 4/1990 | Kwiatek et al. | 128/155 |

OTHER PUBLICATIONS

Johnson & Johnson tape catalog, pages 18 and 19 (describing Dermiclear Transparent Tape, Zonas Porous Tape; Johnson's Waterproof Tape, Elastikon Elastic Tape) (Exhibit A).
Kendall Healthcare Products Co. catalog; pp. 3-35 entitled "Medical Adhesive Tapes" (Exhibit B).
Dale Medical Products, Inc. brochure entitled "Dale Endotracheal Tube Holder" (Exhibit C).
B&B Medical Technologies, Inc. brochure entitled "Secure Solutions" (Exhibit D).

*Primary Examiner*—Aaron J. Lewis
*Attorney, Agent, or Firm*—Jones, Askew & Lunsford

[57] ABSTRACT

Endotracheal tube tape, comprising pre-cut split ends, peel-away tabs, and a guide which are pre-assembled and ready for use. The endotracheal tube tape will secure and stabilize an endotracheal tube, which will ease the minds of many health care workers. The design allows the endotracheal tube tape to be applied rapidly without sacrificing its purpose, which will be valued in emergency situations.

2 Claims, 1 Drawing Sheet

ENDOTRACHEAL TUBE TAPE

BACKGROUND OF THE INVENTION

1. Field of the Invention

The invention is a device for stabilizing and securing an endotracheal tube in a patient who is orally or nasally intubated.

2. Description of Prior Art

Endotracheal tube tape currently on the market has only one strip of tape which wraps the endotracheal tube. Due to the design of the prior art it is undersirable because of its inability to confidently secure the endotracheal tube. The difficulty in properly applying the prior art also makes it undersirable. The ease of application, stability and security of the endotracheal tube is vital because most endotracheal tubes are inserted during emergency situations. This invention eliminates these problems.

SUMMARY OF THE INVENTION

This invention is a device which allows an endotracheal tube to be secured and stabilized with ease. It incorporates the use of a guide to position the tape rapidly and easily. It has two split ends, which provide four strips of tape to wrap the endotracheal tube.

It is an object of the invention to provide an inexpensive device which will allow an endotracheal tube to be safely secured with minimal effort, thus allowing ease of worry and concern for many health care workers.

BREIF DESCRIPTION OF THE DRAWINGS

Figure 1:
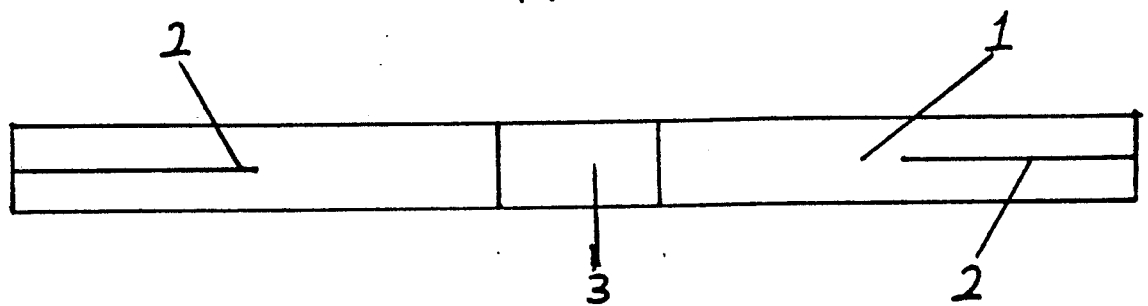
FIG. 1 is a plan view showing the adhesive side of the tube tape without the peel-away tabs.
Figure 2:
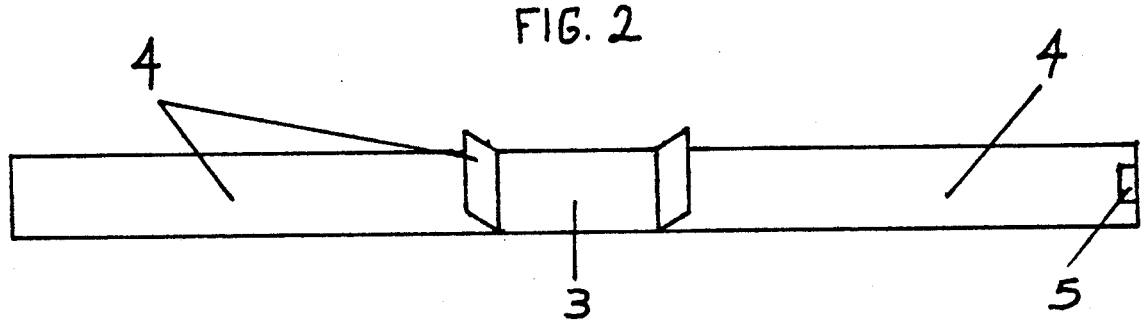
FIG. 2 is a plan view showing the endotracheal tube tape with the peel-away tabs attached to the adhesive side.
Figure 3:
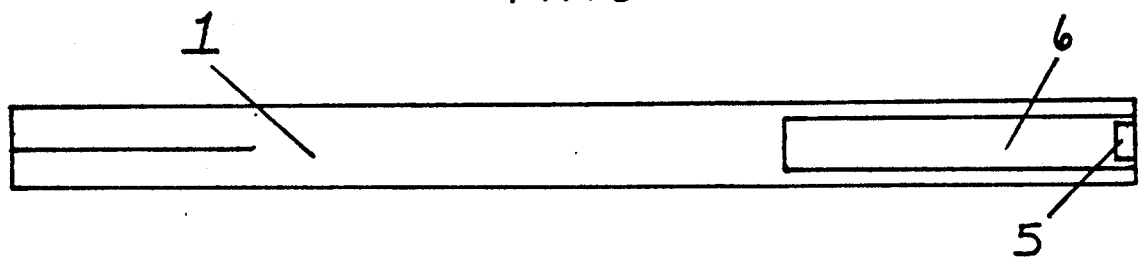
FIG. 3 is a bottom view showing the non-adhesive side of the endotracheal tube tape with the guide intact.
Figure 4:
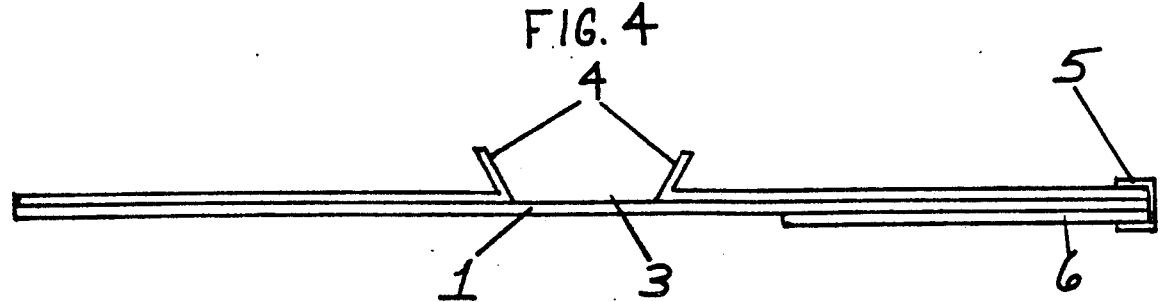

FIG. 4 is a side view showing the endotracheal tube tape with all embodiments intact. The peel-away tab being the top portion, the endotracheal tube tape being the middle portion and the guide being the lower right portion. This view also shows the small portion of tape which connects the guide and the peel-away tab to the endotracheal tube tape.

DESCRIPTION OF THE PREFERRED EMBODIMENT

Referring to the FIGS. 1, 2, 3 and 4 an embodiment of the endotracheal tube tape is shown. In this embodiment several outstanding features are shown. These features include two peel-away tabs (4), two split ends (2), and a guide (6). Other features include a non-adhesive area for the neck (3) and a connective tab (5) which connects the guide (6) and one peel-away tab (4).

In FIG. 4 the endotracheal tube tape is shown with all embodiments attached. With all embodiments attached the endotracheal tube tape is ready for use. With peel-away tab (4) side turned up the endotracheal tube tape is advanced under the neck by the use of the guide (6). The guide (6) is very unique and is a valuable asset to the invention. It allows the endotracheal tube tape (1) to be positioned quickly and easily, which is very important in emergency situations. When the endotracheal tube tape is in place the peel-away tabs (4) are removed. The peel-away tabs (4) are also a unique and valuable asset because they protect the adhesive side of the endotracheal tube tape from blood, salava, prespiration and other contaminants frequently found while securing endotracheal tubes. Due to the connecting tab, (5) when the peel-away tab (4) is removed, the guide (6) is also released and removed.

With the endotracheal tube tape (1) in position the peel-away tabs (4), connecting tab, (4) and guide (6) are removed. The endotracheal tube tape (1). The two split ends (2) are positioned up both sides of the face meeting at the endotracheal tube. The four strips of tape are then wrapped around the endotracheal tube to safely and easily secure the tube in place. The two split ends (2) are a valuable characteristic because they can be adapted easily to different facial and jaw anatomy. The two split ends allow the endotracheal tube to be secured safely without discomfort to the patient or time consuming efforts of the practitioner.

Although one detailed embodiment of the invention is illustrated in the drawings and previously described in detail this invention contemplates any configuration, design and relationship of components which will function in a similar manner and which will provide the equivalent result.

I claim:

1. An apparatus for securing an endotracheal tube, comprising:
    an elongate strip of adhesive tape, including an adhesive side and a non-adhesive side, adhesive side including a central non-adhesive portion and a pair of outer adhesive portions covered with removable protective tabs and extending from said central portion to ends of said strip;
    at least one elongate guide member positioned along the non-adhesive side of said strip adjacent to one of said ends of said strip; and
    means extending around said one end of said strip for connecting said guide member to one of said protective tabs, such that said guide member is removed from said strip along with said one protective tab.

2. The apparatus of claim 1, wherein said outer adhesive portions of said strip are divided into split ends extending from the ends of said strip longitudinally to a point intermediate said ends of said strip and said central portion, said split ends being divided sufficiently close to said central portion such that when said central portion is placed under a patient's neck, said split ends are adhered up both sides of the patient's face.

* * * * *